United States Patent [19]

Mortazavi et al.

[11] Patent Number: 5,556,420

[45] Date of Patent: Sep. 17, 1996

[54] INPUT PROTECTION CIRCUIT FOR PACEMAKER ACTIVITY SENSOR PROCESSING CIRCUITRY

[75] Inventors: Said Mortazavi, Sherman Oaks; Alan Vogel, Saugus, both of Calif.

[73] Assignee: Pacesetter, Inc., Sylmar, Calif.

[21] Appl. No.: 365,667

[22] Filed: Dec. 29, 1994

[51] Int. Cl.$^6$ ..................................................... A61N 1/36
[52] U.S. Cl. ................................................................. 607/9
[58] Field of Search ................................. 607/19, 9, 17

[56] References Cited

U.S. PATENT DOCUMENTS

| | | | |
|---|---|---|---|
| 4,745,923 | 5/1988 | Winstrom | 607/9 |
| 5,074,302 | 12/1991 | Poore et al. | 607/19 |

OTHER PUBLICATIONS

Hodges, David A. et al., *Analysis and Design of Digital Integrated Circuits*, pp. 45–47 (McGraw–Hill, New York–1988).

*Primary Examiner*—William E. Kamm
*Assistant Examiner*—Scott M. Getzow
*Attorney, Agent, or Firm*—Harold C. Schloss; Lisa P. Weinberg

[57] ABSTRACT

An improved input protection circuit for use in a circuit for processing sensor signals from a piezoelectric patient activity sensor is provided. The input protection circuit includes a field-effect transistor to prevent the voltage at an input terminal of the processing circuit from rising beyond a first predetermined voltage or falling below a second predetermined voltage. The gate and drain terminals of the transistor are connected to a first of two input terminals of the processing circuit and the source and body terminals are connected to the second terminal. When the voltage at the first terminal rises or falls sufficiently, the transistor conducts current, thereby preventing the voltage from rising or falling further.

32 Claims, 9 Drawing Sheets

INPUT PROTECTION CIRCUIT FOR PACEMAKER ACTIVITY SENSOR PROCESSING CIRCUITRY

BACKGROUND OF THE INVENTION

The present invention relates to implantable cardiac pacemakers, and particularly to pacemakers capable of providing rate-responsive pacing therapy. More particularly, this invention is directed toward an input protection circuit for pacemaker activity sensor processing circuits that does not produce undesirable offset voltages.

A pacemaker is an implantable medical device which delivers electrical stimulation pulses to cardiac tissue to relieve symptoms associated with bradycardia—a condition in which a patient cannot normally maintain a physiologically acceptable heart rate. Early pacemakers delivered stimulation pulses at regular intervals in order to maintain a predetermined heart rate, typically a rate deemed to be appropriate for the patient at rest. The predetermined rate was usually set at the time the pacemaker was implanted, although in more advanced pacemakers, the rate could be set remotely after implantation.

Early advances in pacemaker technology included the ability to sense the patient's natural cardiac rhythm (i.e., the patient's intracardiac electrogram, or "IEGM"). This led to the development of "demand pacemakers"—so named because they deliver stimulation pulses only as needed by the heart. Demand pacemakers are capable of detecting a spontaneous, hemodynamically effective cardiac contraction which occurs within a predetermined time period (commonly referred to as the "escape interval") following a preceding contraction. When a naturally occurring contraction is detected within the escape interval, the demand pacemaker does not deliver a pacing pulse. The ability of demand pacemakers to avoid delivery of unnecessary stimulation pulses is desirable because by doing so, battery life is extended.

Demand pacemakers allow physicians to telemetrically adjust the length of the escape interval, which has the effect of altering the heart rate maintained by the device. However, in early devices, this flexibility only allowed for adjustments to a fixed programmed rate, and did not accommodate patients who required increased or decreased heart rates to meet changing physiological requirements during periods of elevated or reduced physical activity. Therefore, unlike a person with a properly functioning heart, a patient receiving therapy from an early demand pacemaker was paced at a constant heart rate, regardless of the level to which the patient was engaged in physical activity. Thus, during periods of elevated physical activity, the patient was subject to adverse physiological consequences, including light-headedness and episodes of fainting, because the heart rate was forced by the pacemaker to remain constant.

More recently, pacemakers have become available that are capable of adjusting the rate at which pacing pulses are delivered in accordance with a patient's metabolic needs. These devices, known as "rate-responsive pacemakers," typically maintain a predetermined minimum heart rate when the patient is engaged in physical activity at or below a threshold level, and gradually increase the maintained heart rate in accordance with increases in physical activity until a maximum rate is reached. Rate-responsive pacemakers typically include processing and control circuitry that correlates measured physical activity to a desirable heart rate. In many rate-responsive pacemakers, the minimum heart rate, the maximum heart rate, and the transition rates between the minimum heart rate and the maximum heart rate are parameters that may be adjusted to meet the needs of a particular patient.

One approach that has been considered for enabling rate-responsive pacemakers to determine an appropriate heart rate involves measuring a physiological parameter that reflects the level to which the patient is engaged in physical activity. Physiological parameters that have been considered include central venous blood temperature, blood pH level, QT time interval and respiration rate. However, certain drawbacks (such as slow response time, unpredictable emotionally-induced variations, and wide variability across individuals) render the use of these physiological parameters difficult, and accordingly, they have not been widely used in practice.

Rather, most rate-responsive pacemakers employ sensors that transduce mechanical forces associated with physical activity. These activity sensors generally contain a piezoelectric transducing element which generates a measurable electrical potential when a mechanical stress resulting from physical activity is experienced by the sensor. By analyzing the signal from a piezoelectric activity sensor, a rate-responsive pacemaker can determine how frequently pacing pulses should be applied to the patient's heart.

Piezoelectric elements for activity sensors are commonly formed from piezoelectric ceramics, such as quartz or barium titanate. Recently, however, activity sensors have been designed which use thin films of a piezoelectric polymer, such as polyvinylidene fluoride (commonly known by the trademark KYNAR, owned by ATOCHEM North America) as the transducing element, rather than the more commonly used piezoelectric ceramics. Activity sensors so designed are described in, commonly assigned U.S. Pat. No. 5,383,473, entitled "Rate-Responsive Implantable Stimulation Device Having a Miniature Hybrid-Mountable Accelerometer-Based Sensor and Method of Fabrication," and U.S. Pat. No. 5,425,750, entitled "Accelerometer-Based Multi-Axis Physical Activity Sensor for a Rate-Responsive Pacemaker and Method of Fabrication," which are hereby incorporated by reference in their entireties.

The activity sensors described in the above-incorporated patent applications offer significant advantages over sensors which use piezoelectric ceramics. These advantages are largely attributable to the resiliency of the thin polymer films. For example, the piezoelectric polymer films are better able to withstand stresses that may occur during sensor fabrication, thereby reducing the cost and complexity of the fabrication process. In addition, activity sensors which use the polymer films may be designed to respond more aggressively to mechanical stresses resulting from physical activity, so that they provide stronger output signals. Indeed, the output potentials provided by activity sensors that use polyvinylidene fluoride transducing elements typically have magnitudes of about 200 mV (RMS), whereas piezoelectric ceramic sensors provide output potentials which typically have magnitudes of just a few mV (RMS).

Despite the widespread use of piezoelectric sensors in rate-responsive pacemakers for measuring physical activity, certain difficulties remain which have yet to be overcome. One difficulty relates to the conventional use of a pair of diodes as an input protection circuit for the processing and control circuitry. Although such an arrangement effectively protects the processing and control circuitry from electrostatic discharge potentials, as well as abnormally high signals generated by the piezoelectric sensor (as may occur, for example, if the sensor is mishandled during fabrication), the conventional input protection circuit has an undesirable side effect. Specifically, during normal pacemaker operation, a small leakage current flows through one of the diodes while that diode is reverse biased. This small leakage current flows through a large resistance in parallel with the processing and control circuitry. Thus, an undesirable DC offset potential appears across the processing and control circuitry—even in the complete absence of patient activity.

Under most circumstances, the undesirable DC offset potential may be about 26.7 mV. This could result in an erroneously high determination of the patient's activity level by the processing and control circuitry. Of further concern, however, is that the leakage current through the reverse biased diode is highly temperature dependent—doubling about every 9° C. Since the pacemaker is typically implanted just below the patient's skin, the temperature of the pacemaker can vary with the temperature of the external environment. Thus, the magnitude of the offset potential can vary considerably as the leakage current varies with temperature, making the task of accurately processing the sensor signals even more difficult.

What is needed therefore is an improved input protection circuit that allows the processing and control circuitry of a rate-responsive pacemaker to process activity sensor signals more accurately. The improved input protection circuit should be manufacturable in an efficient and cost-effective manner, and it should not have an adverse impact on the size or operation of the pacemaker.

SUMMARY OF THE INVENTION

The disadvantages and limitations of previously known activity sensor signal processing circuits are overcome by the present invention. With this invention, an improved input protection circuit for protecting the processing and control circuitry of a rate-responsive pacemaker from electrostatic discharge potentials and abnormally high activity sensor signals is provided. The input protection circuit of the present invention replaces conventional input protection circuitry which may cause undesirable, temperature-dependent offset potentials to appear across the processing and control circuitry of the pacemaker. Thus, processing and control circuitry incorporating the improved input protection circuit can more accurately measure the patient's activity level using sensor signals provided by a piezoelectric activity sensor. The improved input protection circuit can be efficiently manufactured at low cost.

The rate-responsive pacemaker incorporating the input protection circuit of the present invention may be conventional in several respects. The rate-responsive pacemaker includes a piezoelectric physical activity sensor (preferably one that uses a piezoelectric polymer film as the transducing element, as described in the above-incorporated U.S. Pat. Nos. 5,383,473 and 5,425,750. The signals generated by the piezoelectric activity sensor are received by processing and control circuitry within the pacemaker. The processing and control circuitry uses the sensor signals to determine the patient's activity level. The measured level of physical activity is then used by the processing and control circuitry to select an appropriate heart rate for the patient. The processing and control circuitry causes a pulse generator to maintain the patient's heart rate at the selected rate in a conventional manner (typically by adjusting the escape interval). Pacing pulses are delivered to the patient's heart through pacing leads, which may also be conventional.

The present invention involves the use of a metal-oxide-semiconductor field-effect transistor to prevent the voltage across the input terminals of the processing and control circuitry from rising beyond a first predetermined voltage or falling below a second predetermined voltage. The gate and drain terminals of the transistor are connected to a first of the two input terminals and the source and body terminals are connected to the second input terminal.

When the voltage at the first terminal rises or falls sufficiently, the transistor conducts current, thereby preventing the voltage from rising or falling further. The use of a single transistor across the input terminals of the processing and control circuitry avoids the use of the conventional pair of diodes to protect the processing and control circuitry. By avoiding the diodes, an undesirable temperature-dependent offset voltage, which would otherwise be present at the input of the processing and control circuitry, is eliminated.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE PREFERRED EMBODIMENT

Figure 1:
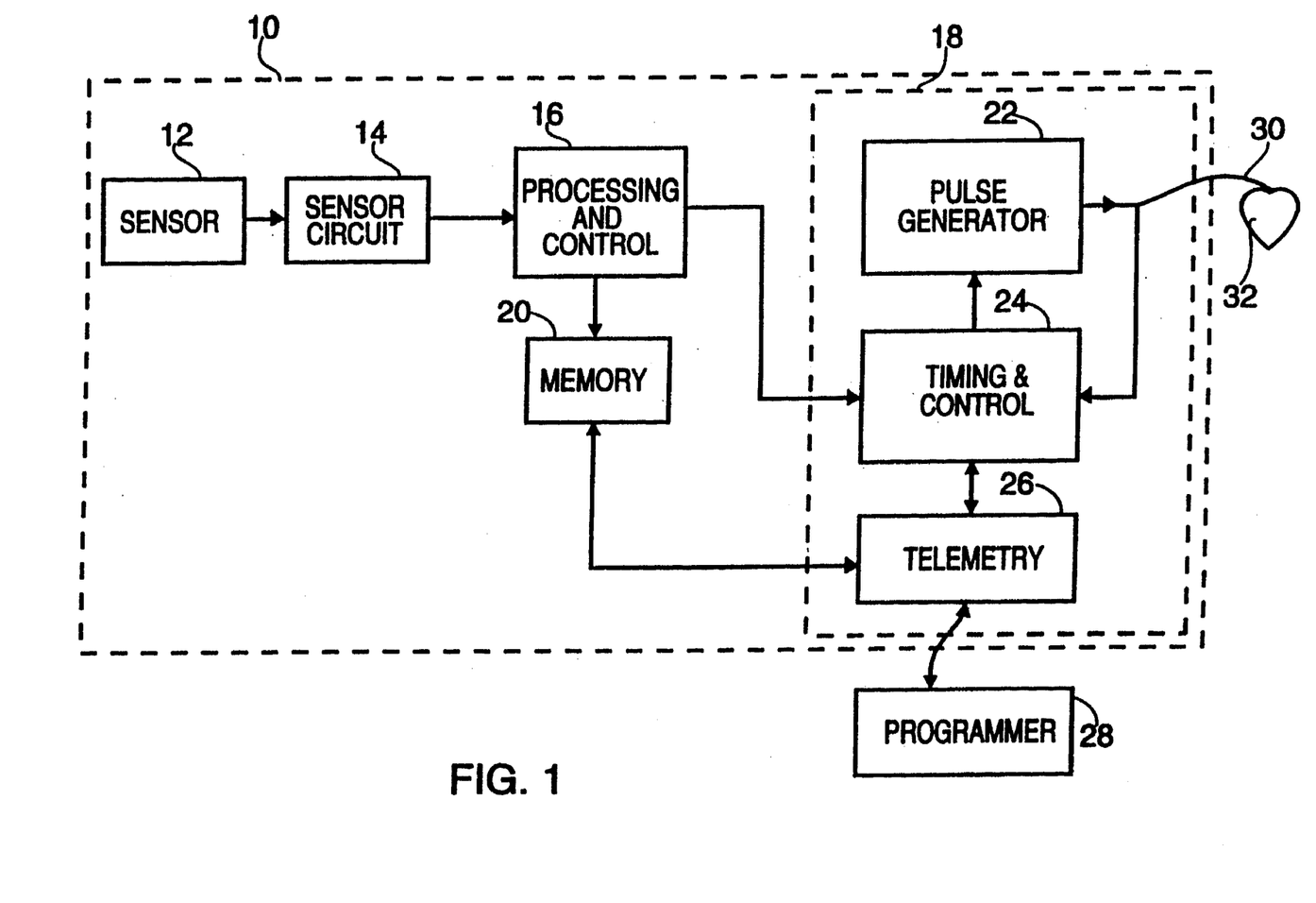
FIG. 1 is a block diagram representing a rate-responsive pacemaker that includes processing and control circuitry that may be adapted to include the input protection circuit of the present invention.

Before describing the details of the input protection circuit of the present invention, a rate-responsive pacemaker 10 shown in FIG. 1 is described so that invention may be understood in context. It should be understood, however, that the input protection circuit of the present invention may be used in other implantable devices, including implantable medical monitoring devices which include piezoelectric physical activity sensors.

In several respects, the pacemaker 10 operates in a conventional manner to provide pacing pulses at a rate that comfortably meets the patient's metabolic demands. More precisely, the pacemaker 10 uses signals generated by a piezoelectric physical activity sensor 12 to determine the extent to which the patient is engaged in physical activity—the measured level of activity being indicative of metabolic need. Preferably, the sensor 12 uses a piezoelectric polymer such as polyvinylidene fluoride as a transducing element (not shown), as described in the above-incorporated U.S. Pat. Nos. 5,383,473 and 5,425,750. However, more traditional piezoelectric materials (not shown) such as quartz or barium titanate may also be used.

The signals generated by the sensor 12 are initially received by a sensor circuit 14. The sensor circuit 14 preferably filters out undesirable low and high frequency signals generated by the sensor 12 and allows signals indicative of patient activity to be received by processing and control circuitry 16.

The pacemaker 10 also includes a pacemaker circuit 18 (which may be conventional) and a memory circuit 20 coupled to the processing and control circuitry 16. The pacemaker circuit 18 includes a pulse generator circuit 22, a timing and control circuit 24 coupled to the pulse generator circuit 22 and to the processing and control circuitry 16, and a telemetry circuit 26. The telemetry circuit 26, which telemetrically communicates with an external programmer 28, is coupled within the pacemaker 10 to the memory circuit 20 and the timing and control circuit 24.

Coupled to the pulse generator circuit 22 is at least one conventional pacing lead 30 (although more pacing leads can be used if needed, as would be the case for a patient receiving dual-chamber pacing therapy). The pacing lead 30 is used to deliver pacing pulses provided by the pulse generator circuit 22 to the patient's heart 32. In addition, the pacing lead 30 senses the natural rhythm of the heart 32 (e.g., the patient's IEGM), and presents a signal indicative thereof to the timing and control circuit 24. The ability to sense the natural rhythm of the heart 32 enables the pacemaker 10 to operate in a demand mode, in which delivery of a pacing pulse is inhibited by the timing and control circuit 24 when a naturally occurring heartbeat is sensed during the escape interval following a preceding contraction.

Although the following description assumes that the pacemaker 10 operates in a demand mode, it should be understood that a simpler implementation is possible, in which the pacemaker 10 does not inhibit delivery of pacing pulses when naturally occurring contractions are sensed. Also, demand pacing may be a telemetrically programmable feature, allowing the pacemaker 10 to be switched into and out of demand mode when desired by a physician.

In operation, the sensor 12 generates electrical potentials when the piezoelectric material of the sensor 12 is mechanically stressed as a result of patient activity. The signals generated by the sensor 12 are initially filtered by the sensor circuit 14, after which they are received by the processing and control circuitry 16.

The processing and control circuitry 16 further processes the sensor signals in order to derive a measurement of the patient's level of physical activity. The processing and control circuitry 16 then uses the processed sensor signals to generate a rate control signal which is provided to the timing and control circuit 24. The timing and control circuit 24 uses the rate control signal to adjust the heart rate maintained by the pacemaker 10. In a preferred embodiment, the rate control signal provided by the processing and control circuitry 16 adjusts the escape interval used by the timing and control circuit 24, which has the effect of increasing or decreasing the maintained heart rate.

Figure 2:
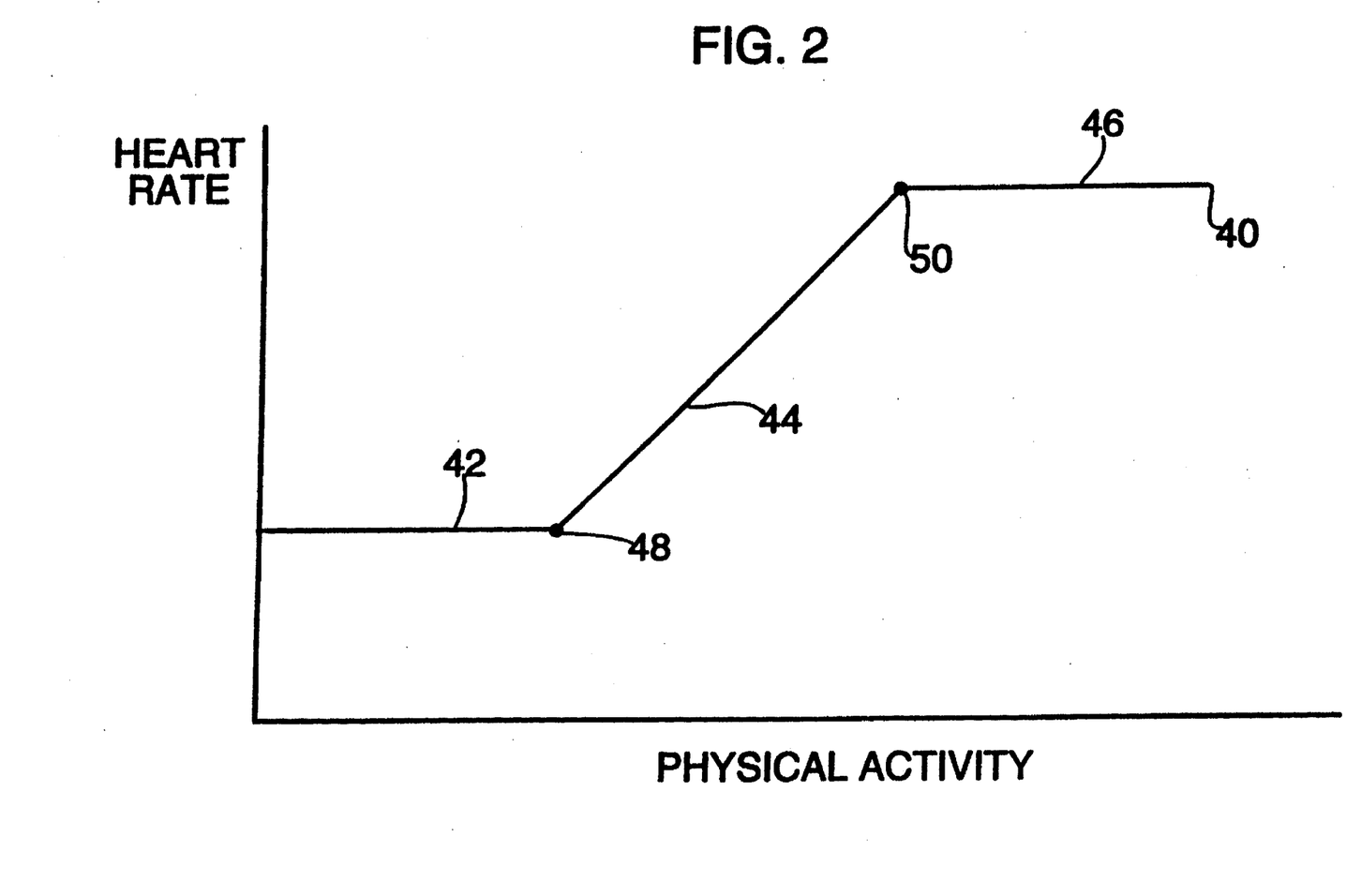
FIG. 2 is an illustrative transfer curve that may be used by the rate-responsive pacemaker of FIG. 1 to correlate measured physical activity to heart rate.

The manner by which the pacemaker 10 adjusts the maintained heart rate in accordance with the signals provided by the sensor 12 may be understood by reference to a transfer curve 40 shown in FIG. 2. The transfer curve 40 correlates physical activity (as measured by the sensor 12 of FIG. 1) along the horizontal axis with a desired heart rate along the vertical axis. The transfer curve 40 has three segments—a minimum rate segment 42, a transition segment 44, and a maximum rate segment 46, each of which may be telemetrically varied to meet the needs of a particular patient. For example, a physician may set the minimum rate segment 42 at 60 beats per minute, and may set a first activity threshold 48 at a relatively low level of physical activity that is required before the pacemaker 10 (FIG. 1) abandons the heart rate defined by the minimum rate segment 42 in favor of a heart rate determined by the transition segment 44. The physician may set the maximum rate segment 46 at, for example, 120 beats per minute, and may set a second activity threshold 50 at a relatively high level of physical activity that is required before the pacemaker 10 (FIG. 1) discontinues using the transition segment 44 in favor of the heart rate corresponding to the maximum rate segment 46. In addition, the transition segment 44 may be telemetrically adjustable, so that changes to the maintained heart rate may be more gradual or more aggressive, depending upon the needs of a particular patient. Further, the shape of the transfer curve 40 may be varied.

Information defining the transfer curve 40 is stored in the memory circuit 20 (FIG. 1) of the pacemaker 10 (FIG. 1) in a conventional manner. For example, the transfer curve 40 may be stored as a collection of discrete data points in a look-up table. Alternatively, the minimum rate segment 42 and the maximum rate segment 46 may be stored discretely, and the transition segment 44 may be stored as a mathematical relationship which is used by the processing and control circuitry 16 (FIG. 1) to compute the heart rate to be maintained when the level of physical activity as measured by the sensor 12 (FIG. 1) falls between the first activity threshold 48 and the second activity threshold 50.

Further details of a pacemaker that includes a conventional input protection circuit are described in connection with FIG. 3. Circuitry 110 of a conventional pacemaker includes an equivalent circuit 112 representing a piezoelectric activity sensor, such as the sensor 12 of FIG. 1. The equivalent circuit 112 includes a voltage source 60, a capacitor 62 (representing the inherent capacitance of the piezoelectric material) of about 6 pF, and a capacitor 64 (representing capacitance contributed by portions of the sensor structure other than the piezoelectric material) of about 2 pF.

The circuitry 110 also includes a resistor network 114 that can serve as the sensor circuit 14 shown in FIG. 1. A resistor 66 in combination with the capacitor 62 form a high-pass filter which blocks undesirable low-frequency signals generated by the sensor 12 (FIG. 1). Preferably, the resistor 66 is fairly large, on the order of 22 GΩ, so that sensor signals that are indicative of patient activity (i.e., those that have frequencies of about 10 Hz) are not blocked. A resistor 68 preferably has a resistance of 4.7 GΩ. The resistor 68 in combination with an approximately 1 pF input capacitance (not shown) of the processing and control circuitry 16 (FIG. 1) forms a low-pass filter that blocks high-frequency noise from the sensor 12 (FIG. 1). Alternatively, the sensor circuit 14 (FIG. 1) can include circuitry to block undesirable, thermally induced signals generated by the sensor 12 (FIG. 1).

The circuitry 110 further includes processing and control circuitry 116 which performs the functions described above for the processing and control circuitry 16 of FIG. 1. The processing and control circuitry 116 includes signal processing circuitry 70, a counter 72, and a microprocessor-based control unit 74. The signal processing circuitry 70 and the counter 72 operate together to provide a measure of the patient's level of physical activity using the signals provided by the sensor 12 (FIG. 1). The control unit 74 uses the measure of physical activity to select an appropriate heart rate for the patient. Rate control signals that define the appropriate heart rate are communicated to the timing and control circuit 24 (FIG. 1) through a pair of output terminals 78 and 80.

Without adequate protection, certain components of the processing and control circuitry 116 may be susceptible to damage if the circuitry 110 is exposed to an electrostatic discharge (ESD) or if the sensor 12 (FIG. 2) generates an abnormally high sensor signal. An ESD may occur, for example, if the processing and control circuitry 116 is mishandled during fabrication of the pacemaker 10 (FIG. 1). An abnormally large signal may be generated by the sensor 12 (FIG. 1) if, for example, the pacemaker 10 (FIG. 1) is accidentally dropped.

To prevent such damage, the processing and control circuitry 116 includes a conventional input protection circuit that consists of a pair of diodes 82 and 84. A power supply (not shown) supplies power to the processing and control circuitry 116 via power supply terminals 86 and 88. A voltage $V_{DD}$ (preferably 0 V) is applied to the power supply terminal 86 and a voltage $V_{SS}$ (preferably −2.8 V) is applied to the power supply terminal 88.

If the circuitry 110 is subjected to an ESD, or if the sensor 12 (FIG. 1) generates an abnormally large AC signal, the voltage at a node 83 is prevented from rising to more than 0.7 V, because at this point the diode 82 is forward biased. Because the voltage drop across the forward-biased diode 82 is effectively pinned at 0.7 V, the diode 82 prevents the voltage at the node 83 from rising, thereby protecting the processing and control circuitry 116 from potentially damaging positive voltage spikes. Similarly, the diode 84 prevents the voltage at the noninverting input of the operational amplifier 76 from falling more than 0.7 V below $V_{SS}$, because at this point diode 84 turns on, thereby pinning the voltage at −3.5 V. The diodes 82 and 84 therefore protect the processing and control circuitry 116 from electrical damage. A resistor 90 of about 1 K Ω is used to prevent an excessive amount of current from flowing through the diodes 82 and 84 in the event that an ESD is applied to the processing and control circuitry 116.

Figure 3:
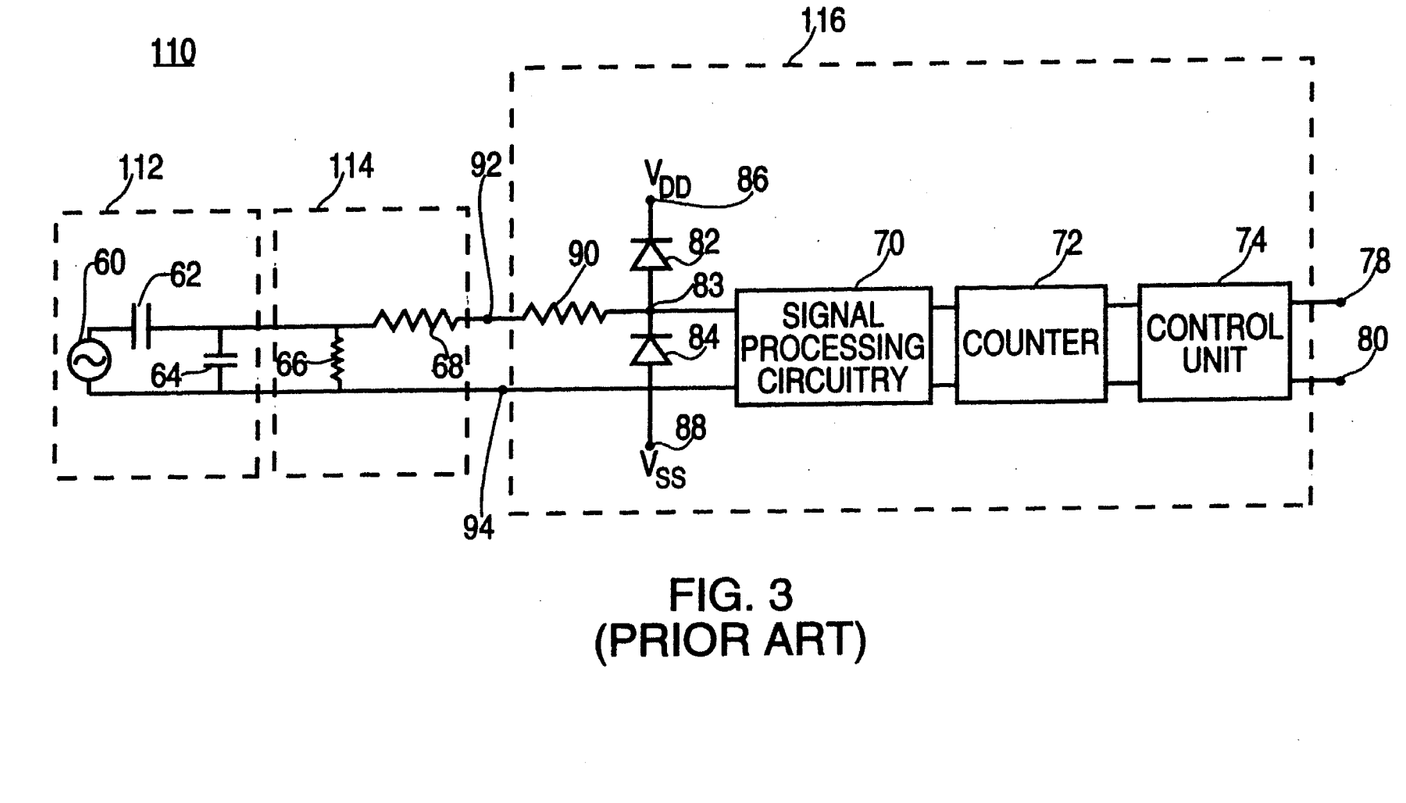
FIG. 3 is a circuit diagram of a portion of a rate-responsive pacemaker that includes a conventional input protection circuit for the processing and control circuitry shown in FIG. 1.

Although the conventional input protection circuit shown in FIG. 3 effectively protects the processing and control circuit 116, in normal operation, the diode 82 is reverse biased. While the diode 82 is reverse biased, a leakage current of approximately 1 pA flows from the power supply terminal 86 to the power supply terminal 88 through the diode 82 and the resistors 90, 68, and 66. The leakage current causes an undesirable DC offset voltage of about 26.7 mV to appear across nodes 92 and 94. (The nodes 92 and 94 may be viewed as input terminals to the processing and control circuitry 116.) This offset voltage is present even in the complete absence of patient activity, and it may thus lead to an erroneously high determination of the patient's activity level. Moreover, the leakage current is highly temperature dependent—doubling every 9° C.— which causes the offset voltage to vary considerably as the temperature of the pacemaker fluctuates.

Figure 4:
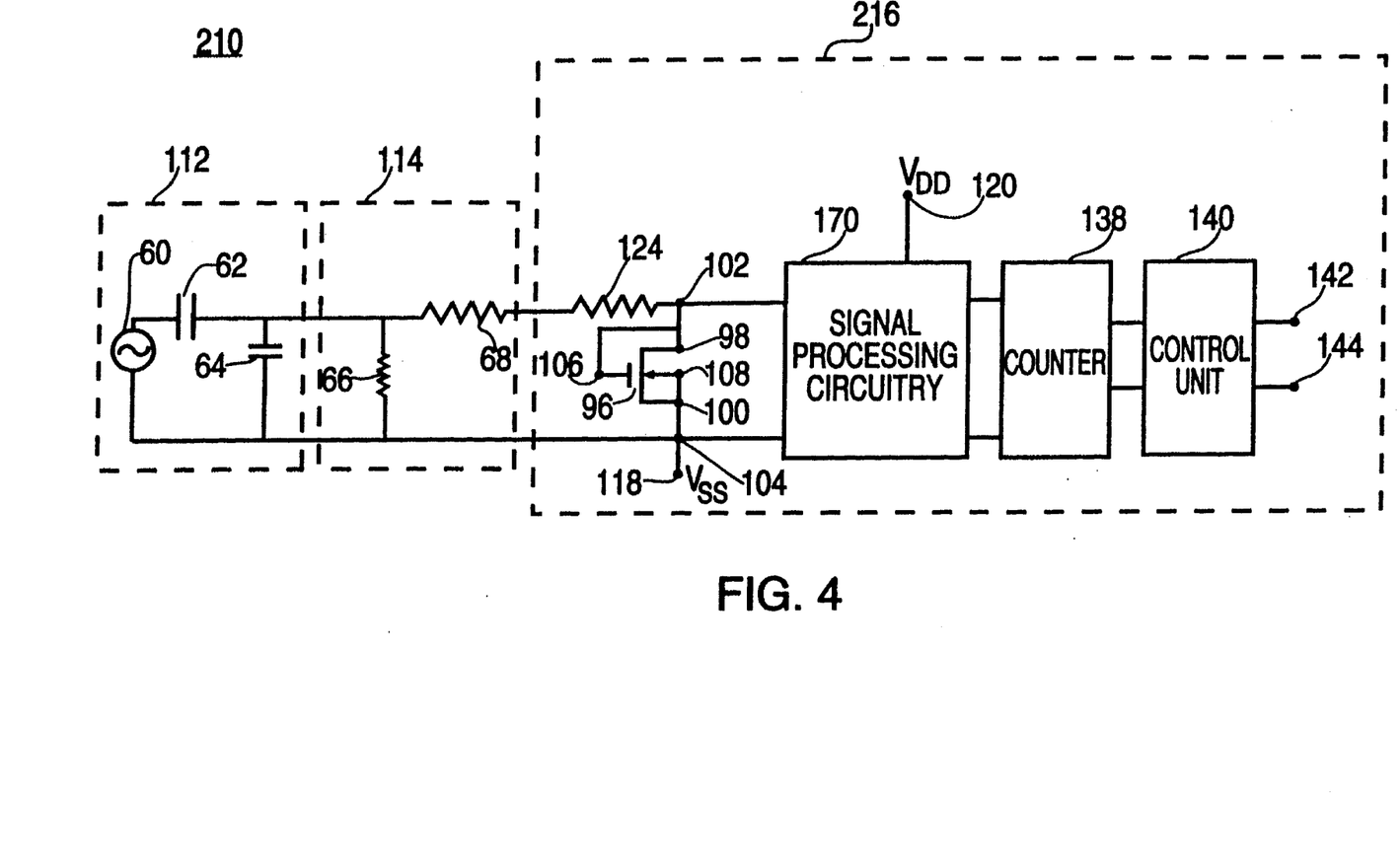
FIG. 4 is a circuit diagram of a portion of a rate-responsive pacemaker that includes an improved NFET-based input protection circuit for processing and control circuitry shown in FIG. 1 in accordance with the principles of the present invention.

An illustrative embodiment of an input protection circuit constructed in accordance with the present invention is shown in FIG. 4. The circuitry 210 of FIG. 4 overcomes the aforementioned drawbacks of the circuitry 110 of FIG. 3. The circuitry 210 preferably includes the equivalent circuit 112 representing a piezoelectric activity sensor (such as the sensor 12 of FIG. 1), and the resistor network 114 (which serves as the sensor circuit 14 of FIG. 1).

The circuitry 210 further includes processing and control circuitry 216 which performs the functions described above with respect to the processing and control circuitry 16 of FIG. 1. However, unlike the conventional processing and control circuitry 116 (FIG. 3), the processing and control circuitry 216 does not require the use of the diodes 82 and 84 (FIG. 3) as input protection circuitry. Instead, the input protection circuit of the present invention is preferably implemented using an metal-oxide-semiconductor field-effect transistor 96 ("FET"). The transistor 96 conducts current when the input voltage between terminals 102 and 104 becomes too large. A resistor 124 (of about 5 K Ω) limits the current through the transistor 96 so that it is not damaged. With this arrangement, the transistor 96 prevents large voltages, such as ESDs and abnormally large sensor signals, from damaging the components within the processing and control circuitry 216.

In some respects the operation of circuitry 210 is similar to that of the conventional arrangement shown in FIG. 3. Signals from a piezoelectric activity sensor (represented by the equivalent circuit 112) are received by the processing and control circuitry 216 via the resistor network 114. Initial processing of the sensor signals is performed by the signal processing circuitry 170, which may be a conventional voltage-controlled oscillator for converting analog signals from the activity sensor to digital pulses. These pulses can be counted by the counter 138 for a predetermined period of time, after which a microprocessor-based control unit 140 can calculate the frequency at which the pulses are generated, which in turn provides a measure of the level of patient activity. The control unit 140 uses this measure of the patient's level of physical activity to select an appropriate heart rate for the patient. Rate control signals that define the appropriate heart rate are communicated to the timing and control circuit 24 (FIG. 1) through a pair of output terminals 142 and 144.

The precise mechanism whereby transistor 96 conducts current in the presence of large voltages varies depending on the type of transistor used. Preferably, the transistor 96 is either an n-channel FET ("NFET") (as shown in FIG. 4) or a p-channel FET ("PFET") (transistor 176 in FIG. 7). The transistors 96 and 176 may be fabricated using complementary metal-oxide-semiconductor ("CMOS") integrated circuit technology. CMOS circuitry is generally preferred for applications involving implanted medical devices, because CMOS circuits exhibit low power consumption. As is well known, CMOS circuits can be implemented using either an n-well or a p-well process. Thus, in a preferred embodiment, transistor 96 may be: (1) an n-well process NFET or (2) a p-well process NFET; transistor 176 may be: (3) an n-well process PFET or (4) a p-well process PFET.

As shown in FIG. 4, the transistor 96 is an NFET having a drain terminal 98 and a source terminal 100 which are connected to the rest of the processing and control circuitry 216 at terminals 102 and 104, respectively. (The terminals 102 and 104 may be viewed as input terminals to the primary functional components of the processing and control circuitry 216.) The transistor 96 also has a gate terminal 106 and a body terminal 108. The gate terminal 106 is connected to the terminal 102 and the body terminal 108 is connected to the terminal 104. Power is supplied to the circuitry 210 via power supply terminals 118 and 120. The voltage at the terminal 118 is $V_{SS}$ (preferably −2.8 V). The voltage at power supply terminal 120 is $V_{DD}$ (preferably 0 V).

Figure 5:
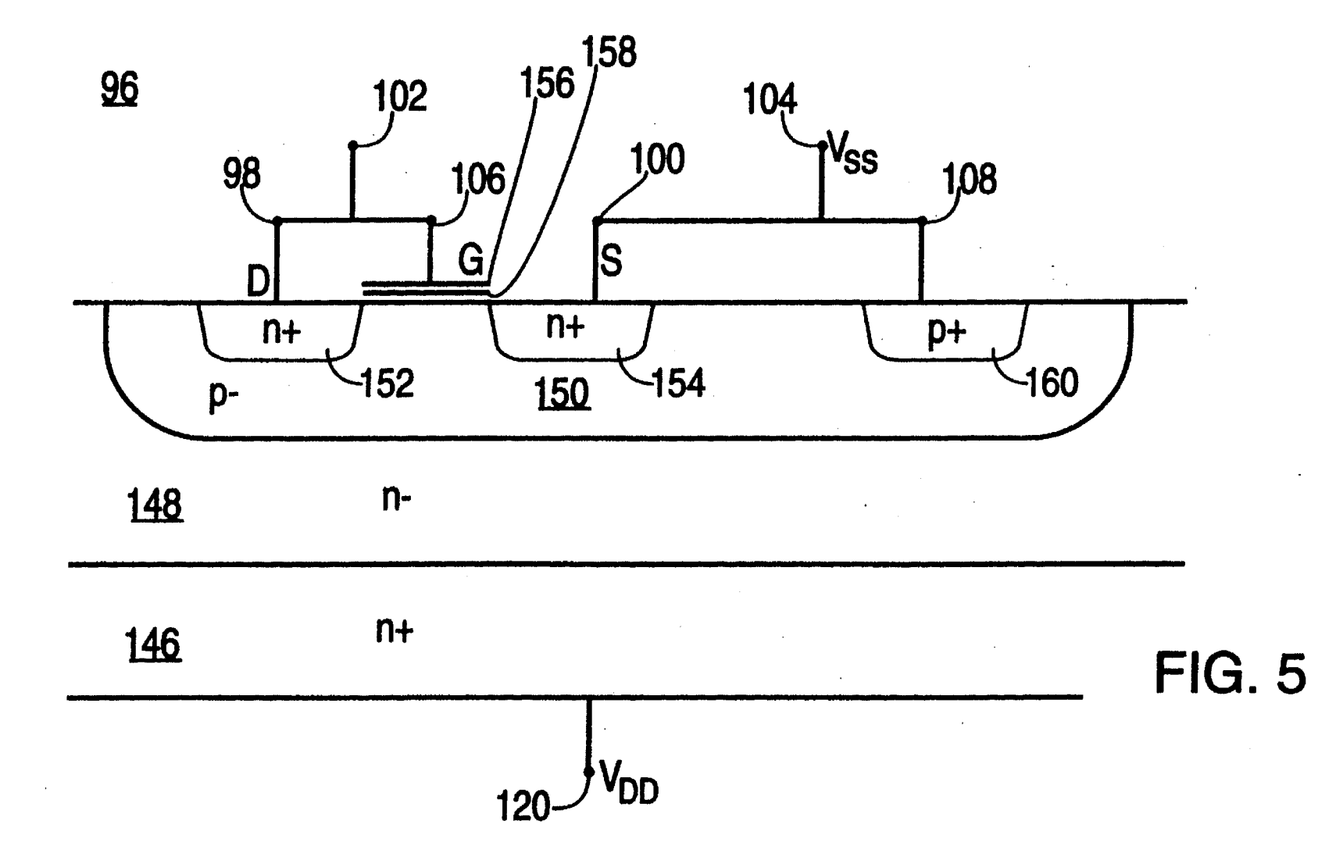
FIG. 5 is a cross-sectional view of an illustrative embodiment of a p-well process NFET structure used to provide input protection in accordance with the principles of the present invention.

A cross-sectional view depicting the physical structure of transistor 96 fabricated using CMOS p-well technology is shown in FIG. 5. As shown in FIG. 5, transistor 96 is formed using an n+ silicon substrate 146, which has a thickness of approximately 200 μm. An approximately 20 μm thick n-epitaxial layer 148 is formed on top of the n+ silicon substrate 146. The PFETs (not shown) of the CMOS structure of FIG. 5 are formed from the n-epitaxial layer 148. The NFETs of the CMOS structure of FIG. 5 are formed in individual p-type wells, such as p-well 150, which is why the arrangement of FIG. 5 is called a "p-well process" structure.

The drain terminal 98 is connected to an n+ region 152 and the source terminal 100 is connected to an n+ region 154. The gate terminal 106 is connected to a gate 156, which is isolated from the p-well 150 using a conventional silicon dioxide layer 158. A p+region 160 is used to provide an ohmic contact between the body terminal 108 and the p-well 150. The n+substrate 146 forms an ohmic contact between the substrate terminal 120 and the n-epitaxial layer 148. The terminal 102 is shown connected to both the drain terminal 98 and the gate terminal 106 of the transistor 96. The voltage $V_{SS}$ is applied to the source terminal 100 and the body terminal 108 at the node 104. When the voltage at the terminal 102 rises to 0.7 V above $V_{SS}$ (i.e., to −2.1 V), the voltage on the gate 156 of the transistor 96 begins to exceed the approximately 0.7 V threshold voltage of the transistor 96 and the transistor 96 will thus turn on. When the transistor 96 is on, current flows between the nodes 102 and 104, which prevents the voltage at the terminal 102 from rising higher than $V_{SS}+0.7$ V (i.e., −2.1 V).

When the voltage at the terminal 102 falls to approximately 0.7 V below $V_{SS}$ (i.e., to −3.5 V), the structure shown in FIG. 5 acts as an active forward-biased bipolar junction transistor, so that current flows between the terminal 102, which is connected to the drain terminal 98, and the substrate terminal 120. Terminals 108, 120, and 98 are analogous to the base, collector, and emitter terminals of an npn bipolar junction transistor. A voltage $V_{DD}$ (0 V) is applied to the n-epitaxial layer 148 via the substrate terminal 120 and the n+ substrate 146, which forms an ohmic contact with the n-epitaxial layer 148. The p-well 150 is maintained at a voltage of $V_{SS}$ (−2.8 V) via the body terminal 108 and the p+ region 160, which forms an ohmic contact with the p-well 150.

With a −2.8 V voltage drop across the p-well 150 and the n-epitaxial layer 148, these layers form a reverse-biased pn junction analogous to the base-collector junction in an npn bipolar junction transistor. Because the drain terminal 98 is at approximately 0.7 V below $V_{SS}$ (i.e., at −3.5 V), the n+ region 152 and the p-well 150 form a forward-biased pn junction, analogous to the emitter-base junction of an npn bipolar transistor. Together, the reverse-biased pn junction formed by the p-well 150 and the n-epitaxial layer 148 and the forward-biased pn junction formed by the n+ region 152 and the p-well 150 act as an active forward-biased npn bipolar junction transistor. The npn bipolar junction transistor conducts current primarily via the terminal 102 (via drain terminal 98) and the substrate terminal 120, thereby effectively limiting the negative extent to which the voltage at the terminal 102 can fall to $V_{SS}$0.7 V (i.e., to −3.5 V).

Thus, the transistor 96 maintains the voltage across terminals 102 and 104 between ±0.7 V of $V_{SS}$ (i.e., −3.5 V to −2.1 V), so that the components of the processing and control circuitry 216 (such as signal processing circuitry 170) are protected from ESDs and excessively large sensor signals.

Figure 6:
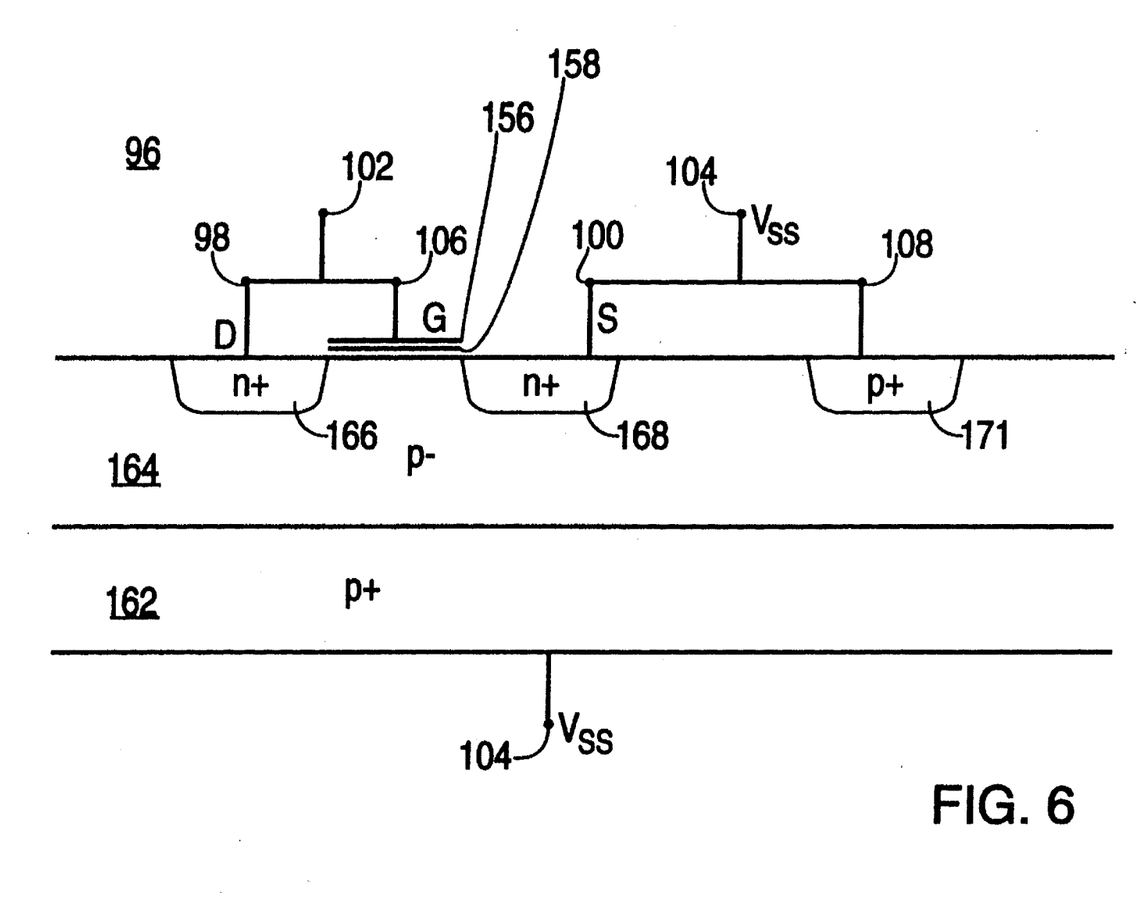
FIG. 6 is a cross-sectional view of an illustrative embodiment of an n-well process NFET structure used to provide input protection in accordance with the principles of the present invention.

If the NFET of FIG. 4 (the transistor 96) uses an n-well process CMOS technology, the physical structure of transistor 96 is as shown in the cross-sectional view of FIG. 6. The transistor 96 shown in FIG. 6 has a p+substrate 162. NFETs are formed from a p-epitaxial layer 164. PFETs are formed from n-wells (not shown). Two n+ regions 166 and 168, make up the drain and source, respectively. An ohmic contact between the terminal 104 and the p-epitaxial layer 164 is formed by a p+ region 171.

When the voltage at terminal 102 is higher than the voltage at terminal 104, the operation of the n-well process NFET structure of FIG. 6 is similar to the p-well process NFET structure of FIG. 5. When the voltage at terminal 102 rises to 0.7 V above $V_{SS}$ (i.e., to −2.1 V), the voltage on the gate 156 of the transistor 96 begins to exceed the approximately 0.7 V threshold voltage of the transistor 96 and the transistor 96 will thus turn on. When the transistor 96 is on, current flows between the nodes 102 and 104, which prevents the voltage at the terminal 102 from rising higher than $V_{SS}+0.7$ V (i.e., −2.1 V).

When the voltage at the terminal 102 is lower than the voltage at the terminal 104, the transistor 96 Of FIG. 6 limits the voltage across the terminals 102 and 104, as is the case with the structure of FIG. 5. However, the conduction mechanism differs. Rather than conducting as an active forward-biased npn bipolar transistor, the transistor 96 of FIG. 6 conducts via a simple pn junction mechanism. As shown in FIG. 6, when the voltage at the terminal 102 drops more than 0.7 V with respect to the voltage at the terminal 104, then the p-epitaxial layer forms a forward biased pn junction with the n+ region 166. Thus, the transistor 96 conducts current between the terminal 104 and the terminal 102 via the p+ substrate 162, the p-epitaxial layer 164, and the n+ region 166. Because the terminal 104 is also ohmically connected to the p-epitaxial layer 164 via the p+ region 171, current may also flow from the terminal 104 to the terminal 102 via the p+ region 171, the p-epitaxial layer 164, and the n+ region 166. Because the transistor conducts current between the terminal 104 and the terminal 102, the voltage between at the terminal 102 is prevented from dropping by more than the turn on threshold of a pn diode (about 0.7 V) below the voltage at the terminal 104.

Figure 7:
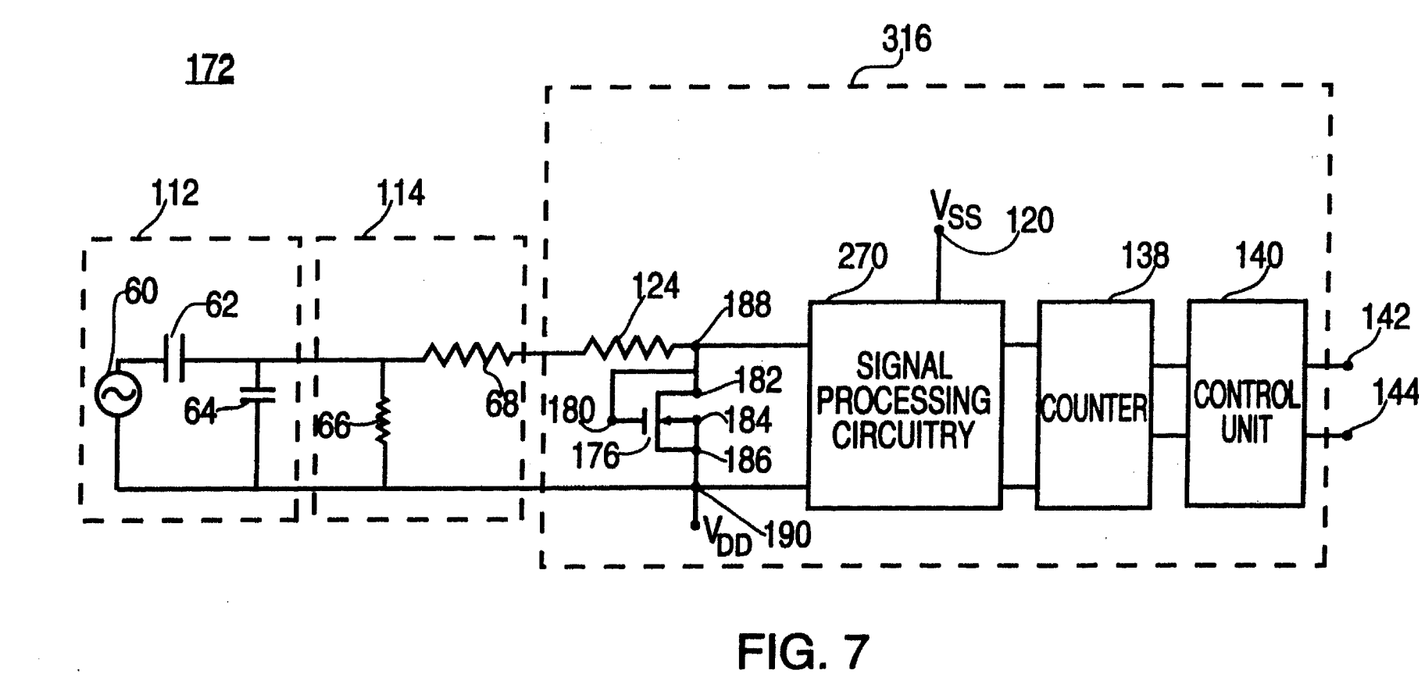
FIG. 7 is a circuit diagram of a portion of a rate-responsive pacemaker that includes an improved PFET-based input protection circuit for processing and control circuitry shown in FIG. 1 in accordance with the principles of the present invention.

If it is desired to use an input protection circuit arrangement that uses a PFET rather than an NFET, then the circuitry 172 of FIG. 7 is used. The circuitry 172 of FIG. 7 is similar in many respects to the circuitry of FIG. 4. For example, the piezoelectric activity sensor (represented by the equivalent circuit 112) is the same, as is the resistor network 114. Also, the counter 138 and the control unit 140 are the same in both arrangements. However, as shown in FIG. 7, processing and control signal circuitry 316 differs from processing and control circuitry 216 (FIG. 4) in that the input protection transistor 176 is a PFET. Accordingly, the supply voltages $V_{SS}$ and $V_{DD}$ are reversed. Signal processing circuitry 270, which may be a conventional voltage-controlled oscillator, performs the same function as the signal processing circuitry 170 of FIG. 4, but is not identical to that circuitry due to the differing voltage polarities. The transistor 176 has its gate 180 connected to its drain 182. A body terminal 184 is connected to a source terminal 186.

Figure 8:
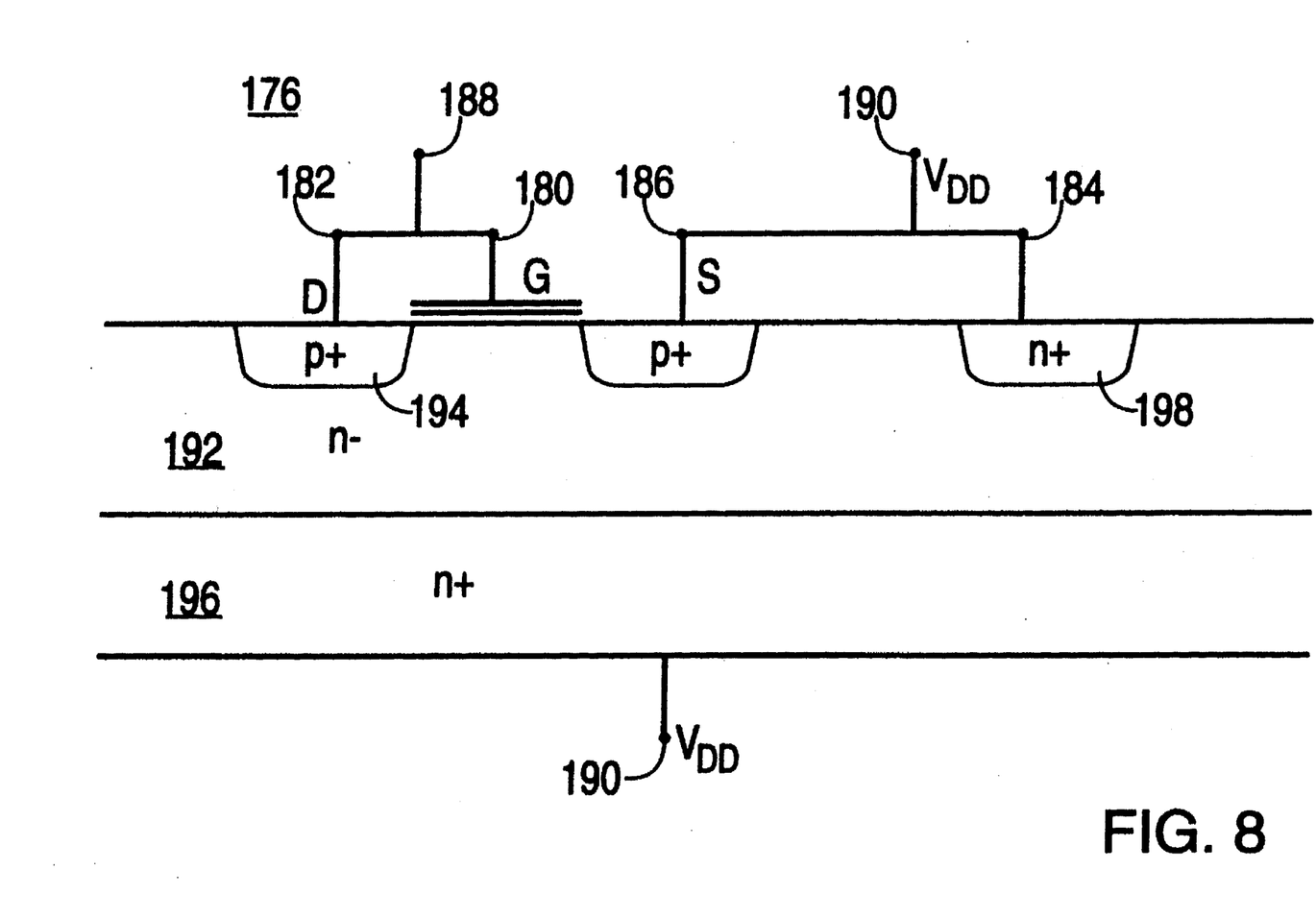
FIG. 8 is a cross-sectional view of an illustrative embodiment of a p-well process PFET structure used to provide input protection in accordance with the principles of the present invention.
Figure 9:
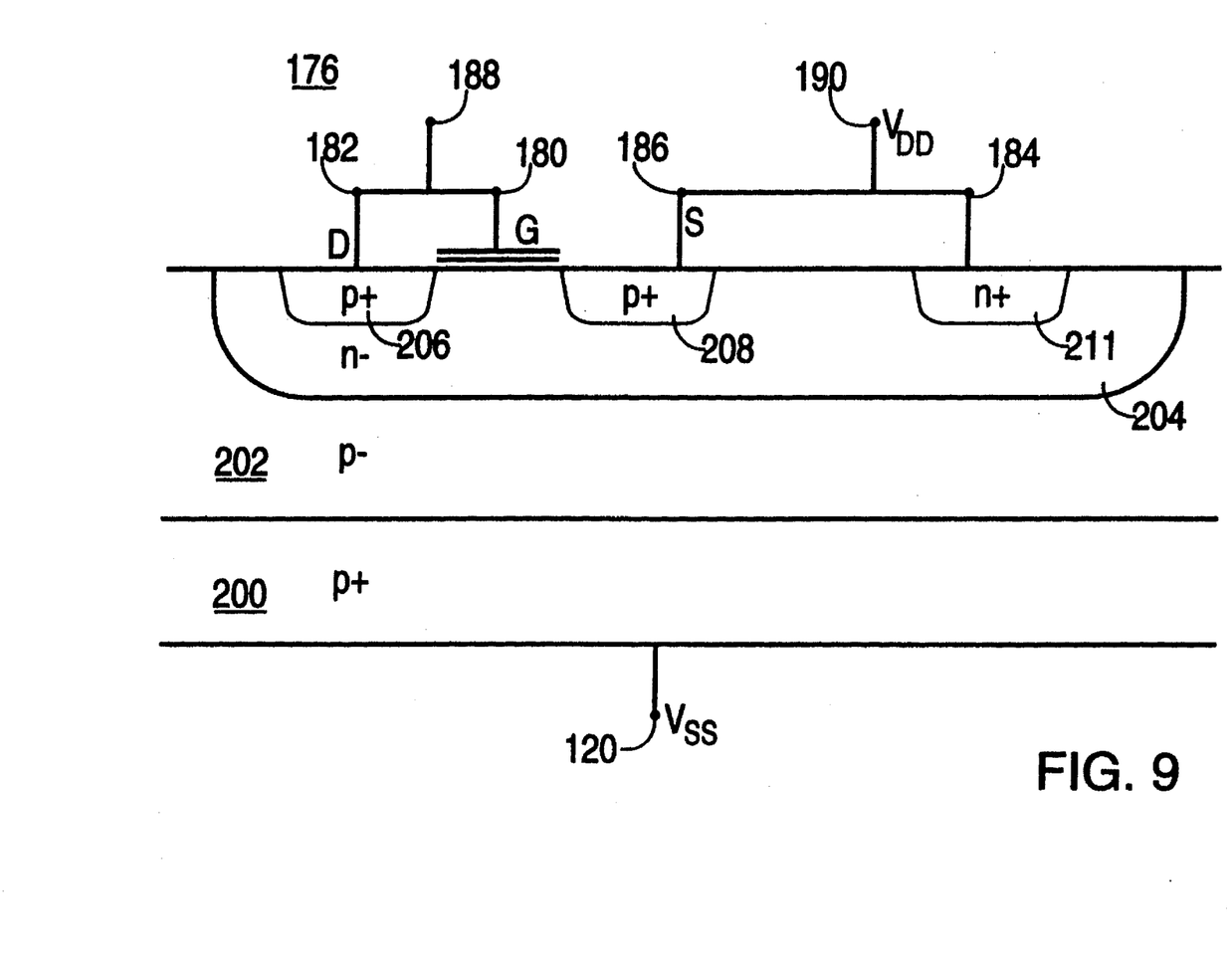
FIG. 9 is a cross-sectional view of an illustrative embodiment of an n-well process PFET structure used to provide input protection in accordance with the principles of the present invention.

The transistor 176 provides input protection by limiting the voltage across terminals 188 and 190 in much the same way as transistor 96 limited the voltage across the terminals 102 and 104. A PFET structure based on a p-well CMOS technology is shown in FIG. 8. A PFET structure based on an n-well CMOS technology is shown in FIG. 9.

The operation of the p-well process PFET structure of FIG. 8 is similar to the n-well process NFET structure of FIG. 6, but with the polarities of the voltages reversed. When the voltage at the terminal 188 rises to more than about 0.7 V greater than the voltage at the terminal 190 ($V_{DD}$), then the p+ region 194 and the n-epitaxial layer 192 form a forward biased pn junction. Thus, the transistor 176 conducts current between the terminal 188 and the terminal 190 via the p+ region 194, the n-epitaxial layer 192, and the n+substrate 196. Because the terminal 190 is also ohmically connected to the n-epitaxial layer 192 via the n+ region 198, current may also flow from the terminal 188 to the terminal 190 via the p+ region 194, the n-epitaxial layer 192, and the n+ region 198. Because the transistor conducts current between the terminal 188 and the terminal 190, the voltage at the terminal 188 is prevented from rising by more than the turn on threshold of a pn diode (about 0.7 V).

When the voltage at the terminal 188 is lower than the voltage at terminal 190 by about 0.7 V, the voltage on the gate 188 of the transistor 176 begins to turn on the transistor 176. When the transistor 176 is on, current flows between the terminals 188 and 190, which prevents the voltage at the terminal 188 from falling below $V_{DD}$–0.7 V.

When the transistor 176 is a PFET formed using an n-well process CMOS technology, its operation is similar to the operation of the p-well NFET of FIG. 5, but with the polarities reversed. As shown in FIG. 9, when implemented using an n-well process, the transistor 176 has a p+ substrate 200 and a p-epitaxial layer 202. An n-well 204 is formed within the epitaxial layer 202. Drain and source contacts are formed by p+ regions 206 and 208, respectively. An ohmic contact to the n-epitaxial layer is formed via n+ region 211.

When the voltage at terminal 188 rises more than about 0.7 V relative to the voltage at the terminal 190, the structure of FIG. 9 forms an active forward biased pnp bipolar transistor, conducting current primarily between the terminals 188 and 120, and thereby preventing the voltage at terminal 188 from rising. When the voltage at terminal 188 drops more than about 0.7 V relative to the voltage at the terminal 190, the transistor 176 turns on. As the transistor 176 turns on, current is conducted between the terminals 188 and 190, which prevents the voltage at the terminal 188 from dropping further.

Thus it is seen that an improved input protection circuit for use in a circuit for processing sensor signals from a piezoelectric physical activity sensor is provided. The input protection circuit allows the sensor signal processing circuit to more accurately process sensor signals by eliminating circuitry that previously produced an undesirable temperature-dependent offset voltage. The arrangement of the present invention involves the use of a field-effect transistor to prevent the voltage at the input of the processing circuit from rising beyond a first predetermined voltage or falling below a second predetermined voltage. The gate and drain terminals of the transistor are connected to a first of two input terminals of the processing circuit and the source and body terminals are connected to the second terminal. When the voltage at the first terminal either rises or falls sufficiently with respect to the second terminal the transistor conducts current, thereby preventing the voltage from rising or falling further. The use of a single transistor across the input terminals of the processing circuitry avoids the use of a pair of diodes to protect the processing circuitry. By avoiding such diodes, an undesirable temperature-dependent offset voltage, which would otherwise be present at the input of the processing circuitry, is eliminated.

One skilled in the art will appreciate that the present invention can be practiced by other than the described embodiments, which are presented for purposes of illustration and not of limitation, and the present invention is limited only by the claims that follow.

What is claimed is:

1. A rate responsive pacemaker, comprising:
 a pulse generator for generating pacing pulses at an adjustable rate;
 a physiologic sensor for providing signals indicative of metabolic demand;
 a processing and control circuit, coupled to the pulse generator and the physiologic sensor, for determining the rate at which the pulse generator generates pacing pulses in accordance with the signals provided by the physiologic sensor; and
 a transistor circuit, coupled to the processing and control circuit and the physiologic sensor, for protecting the processing and control circuit from voltages generated by the physiological sensor that are greater than a first threshold and less than a second threshold.

2. The pacemaker of claim 1, wherein the transistor circuit comprises a field-effect transistor.

3. The pacemaker of claim 2, wherein the field effect transistor is an n-channel metal-oxide-semiconductor field-effect transistor.

4. The pacemaker of claim 3, wherein the transistor circuit uses n-well process CMOS technology.

5. The pacemaker of claim 3, wherein the transistor circuit uses p-well process CMOS technology.

6. The pacemaker of claim 2, wherein the field effect transistor is a p-channel metal-oxide-semiconductor field-effect transistor.

7. The pacemaker of claim 6, wherein the transistor circuit uses n-well process CMOS technology.

8. The pacemaker of claim 6, wherein the transistor circuit uses p-well process CMOS technology.

9. The pacemaker of claim 1, wherein the physiologic sensor comprises a physical activity sensor.

10. The pacemaker of claim 9, wherein the physical activity sensor comprises a piezoelectric element.

11. The pacemaker of claim 10, wherein the piezoelectric element comprises polyvinylidene fluoride.

12. A rate-responsive pacemaker, comprising:
 a piezoelectric activity sensor;
 activity sensor processing circuitry comprising:
  first and second input terminals for receiving signals of varying magnitudes from the activity sensor;
  first and second power supply terminals maintained respectively, at first and second power supply voltages; and
  first and second output terminals;
 wherein the processing circuitry processes the sensor signals to generate output pulses at the first and second output terminals at frequencies proportional to the magnitudes of the sensor signals; the pacemaker further comprising:

a counter for counting the output pulses for a predetermined period of time;

a control unit for calculating the frequency at which the pulses are generated; and input protection circuitry for protecting the activity sensor signal processing circuitry from excessively large voltages, the input protection circuitry including a field-effect transistor comprising:

a drain terminal connected to the first input terminal of the processing circuitry, a gate terminal connected to the first input terminal of the processing circuitry, a source terminal connected to the second input terminal of the processing circuitry and the first power supply terminal, a body terminal connected to the second input terminal; and a substrate terminal connected to the second power supply terminal, wherein:

when a voltage exceeding a first threshold appears at the first input terminal, the transistor turns on, thereby conducting current between the drain and source terminals and preventing a substantially higher voltage from developing at the first input terminal; and when a voltage less than a second threshold appears at the first input terminal, the transistor acts as an active forward-biased bipolar junction transistor, conducting current between the drain and substrate terminals and preventing a substantially lower voltage from developing at the first input terminal.

13. The pacemaker of claim 12, further comprising a resistor coupling the transistor to the activity sensor.

14. The pacemaker of claim 12, wherein the activity sensor comprises polyvinylidene fluoride.

15. The pacemaker of claim 12, wherein the first threshold is equal to the sum of the first power supply voltage and a transistor turn-on voltage.

16. The pacemaker of claim 12, wherein the second threshold is equal to the first power supply voltage less a pn junction turn-on voltage.

17. An implantable medical device, comprising:

a physiologic sensor;

a processing and control circuit, coupled to the physiologic sensor; and a transistor circuit, coupled to the processing and control circuit and the physiologic sensor, for protecting the processing and control circuit from voltages generated by the physiological sensor that are greater than a first threshold.

18. The implantable medical device of claim 17, wherein the transistor circuit protects the processing and control circuit from voltages generated by the physiological sensor that are less than a second threshold.

19. The implantable medical device of claim 17, wherein the transistor circuit comprises a field-effect transistor.

20. The implantable medical device of claim 17, wherein the transistor circuit uses n-well process CMOS technology.

21. The implantable medical device of claim 17, wherein the transistor circuit uses p-well process CMOS technology.

22. The implantable medical device of claim 17, wherein the physiologic sensor comprises a physical activity sensor.

23. The implantable medical device of claim 13, wherein the physiologic sensor comprises a piezoelectric element.

24. The implantable medical device of claim 23, wherein the piezoelectric element comprises polyvinylidene fluoride.

25. An implantable medical device, comprising:

a physiologic sensor;

a processing and control circuit, having first and second input terminals for receiving signals from the physiologic sensor; and input protection apparatus for protecting the processing and control circuit of the implantable medical device from excessively large voltages generated by the physiologic sensor, the input protection apparatus comprising a field-effect transistor having a drain and a gate connected to the first input terminal and a source and a body connected to the second input terminal, wherein:

when a voltage exceeding a first threshold appears at the first input terminal, the transistor conducts current, thereby preventing a substantially higher voltage from developing at the first input terminal; and when a voltage less than a second threshold appears at the first input terminal, the transistor conducts current, thereby preventing a substantially lower voltage from developing at the first input terminal.

26. The implantable medical device of claim 25, wherein the input protection apparatus further comprises a resistor coupling the transistor to the physiologic sensor.

27. The implantable medical device of claim 25, wherein the physiologic sensor comprises a piezoelectric element that generates the sensor signals.

28. The implantable medical device of claim 27, wherein the piezoelectric element comprises polyvinylidene fluoride.

29. The implantable medical device of claim 25, wherein the transistor is an n-channel metal-oxide-semiconductor field-effect transistor.

30. The implantable medical device of claim 25, wherein the transistor uses n-well process CMOS technology.

31. The implantable medical device of claim 25, wherein the transistor uses p-well process CMOS technology.

32. The implantable medical device of claim 25, wherein the transistor is a p-channel metal-oxide-semiconductor field-effect transistor.

* * * * *